US012631585B2

(12) United States Patent
Kaita et al.

(10) Patent No.: US 12,631,585 B2
(45) Date of Patent: May 19, 2026

(54) GAS SENSOR

(71) Applicant: TDK Corporation, Tokyo (JP)

(72) Inventors: Yoshio Kaita, Tokyo (JP); Yasuhiro Inui, Tokyo (JP); Yutaka Matsuo, Tokyo (JP)

(73) Assignee: TDK Corporation, Tokyo (JP)

( * ) Notice: Subject to any disclaimer, the term of this patent is extended or adjusted under 35 U.S.C. 154(b) by 284 days.

(21) Appl. No.: 18/482,431

(22) Filed: Oct. 6, 2023

(65) Prior Publication Data

US 2024/0133834 A1    Apr. 25, 2024
US 2024/0230570 A9    Jul. 11, 2024

(30) Foreign Application Priority Data

Oct. 19, 2022    (JP) ................................. 2022-167731
Jul. 6, 2023    (JP) ................................. 2023-111146

(51) Int. Cl.
*G01N 27/12*    (2006.01)
*G01N 27/18*    (2006.01)
*G01N 33/00*    (2006.01)

(52) U.S. Cl.
CPC ........... *G01N 27/122* (2013.01); *G01N 27/18* (2013.01); *G01N 33/004* (2013.01); *G01N 33/0068* (2024.05); *G01N 33/0073* (2013.01)

(58) Field of Classification Search
CPC .... G01N 27/122; G01N 27/18; G01N 33/004; G01N 33/0068; G01N 33/0073
See application file for complete search history.

(56) References Cited

U.S. PATENT DOCUMENTS

| | | | | |
|---|---|---|---|---|
| 6,526,801 | B2 * | 3/2003 | Kouznetsov | ....... G01N 33/0006 |
| | | | | 73/1.03 |
| 2006/0173637 | A1 * | 8/2006 | Martin | ............... G01N 33/0006 |
| | | | | 702/24 |
| 2019/0033274 | A1 * | 1/2019 | Makaram | ........... G01N 33/0008 |

FOREIGN PATENT DOCUMENTS

| | | |
|---|---|---|
| JP | 09-015178 A | 1/1997 |
| JP | 2010-085339 A | 4/2010 |
| JP | 2015-224892 A | 12/2015 |
| JP | 2017-156293 A | 9/2017 |
| JP | 2019-105487 A | 6/2019 |

* cited by examiner

*Primary Examiner* — Paul M. West
(74) *Attorney, Agent, or Firm* — Rimon P.C.

(57) ABSTRACT

Disclosed herein is a gas sensor that includes a sensor part configured to generate a gas detection signal in accordance with a concentration of a gas to be measured, and a control circuit configured to generate an output signal indicating the concentration of the gas to be measured based on the gas detection signal. The control circuit is configured to correct the output signal so that the output signal indicates a concentration of the gas to be measured higher than that indicated by the gas detection signal when a level of the gas detection signal output from the sensor part is less than a reference value corresponding to a level of the gas detection signal which is normally obtained when a concentration of the gas to be measured is a concentration value in normal time.

15 Claims, 5 Drawing Sheets

GAS SENSOR

CROSS-REFERENCE TO RELATED APPLICATION

This application claims the benefit of Japanese Patent Application No. 2022-167731, filed on Oct. 19, 2022, and Japanese Patent Application No. 2023-111146, filed on Jul. 6, 2023, the entire disclosure of which are incorporated by reference herein.

BACKGROUND OF THE ART

Field of the Art

The present disclosure relates to a gas sensor.

Description of Related Art

JP 2017-156293A discloses a gas sensor that calculates the concentration of gas to be measured based on the level of a signal appearing at the connection point between two series-connected thermistors. In the gas sensor described in JP 2017-156293A, the two thermistors are heated to mutually different temperatures to acquire a first output value and are then heated to the same temperature to acquire a second output value, and the first output value is corrected based on the second output value to thereby cancel the influence of drift caused due to a temporal change.

However, in the gas sensor described in JP 2017-156293A, it is necessary to heat the thermistors multiple times every time gas concentration measurement is performed, disadvantageously increasing power consumption.

SUMMARY

It is desirable to provide an improved gas sensor capable of canceling the influence of drift.

A gas sensor according to the present disclosure includes a sensor part configured to generate a gas detection signal in accordance with a concentration of a gas to be measured, and a control circuit configured to generate an output signal indicating the concentration of the gas to be measured based on the gas detection signal. The control circuit is configured to correct the output signal so that the output signal indicates a concentration of the gas to be measured higher than that indicated by the gas detection signal when a level of the gas detection signal output from the sensor part is less than a reference value corresponding to a level of the gas detection signal which is normally obtained when a concentration of the gas to be measured is a concentration value in normal time.

BRIEF DESCRIPTION OF THE DRAWINGS

The above features and advantages of the present disclosure will be more apparent from the following description of certain preferred embodiments taken in conjunction with the accompanying drawings, in which.

DETAILED DESCRIPTION OF THE EMBODIMENTS

Preferred embodiments of the present disclosure will be explained below in detail with reference to the accompanying drawings.

Figure 1:
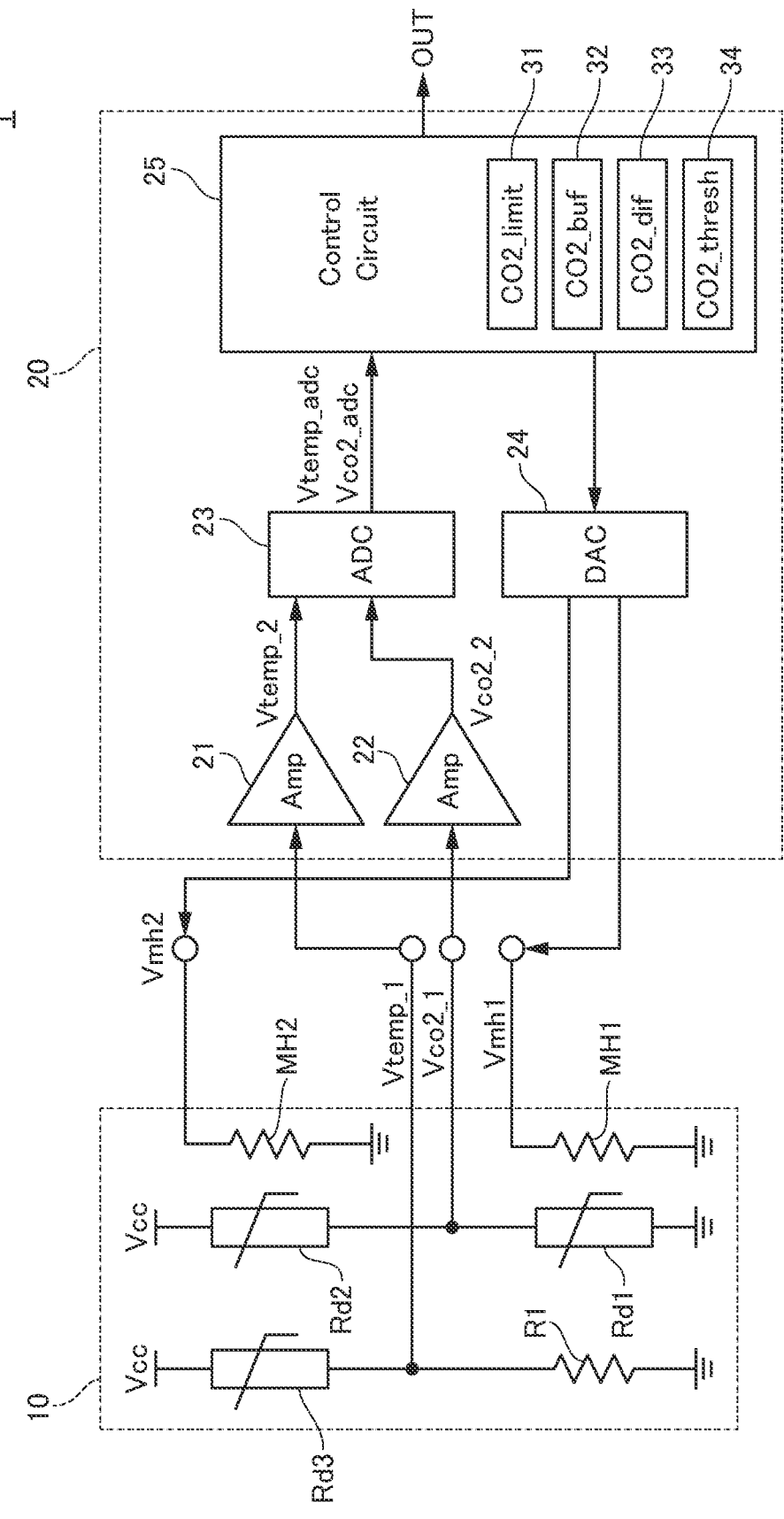
FIG. 1 is a circuit diagram illustrating the configuration of a gas sensor 1 according to one embodiment of the technology relevant to the present disclosure.

FIG. 1 is a circuit diagram illustrating the configuration of a gas sensor 1 according to one embodiment of the technology relevant to the present disclosure.

As illustrated in FIG. 1, the gas sensor 1 according to the present embodiment has a sensor part 10 and a control circuit 20. Although not particularly limited, the gas sensor 1 according to the present embodiment is configured to detect the concentration of $CO_2$ gas in the atmosphere.

The sensor part 10 is constituted by a heat conduction type gas sensor for measuring the concentration of $CO_2$ gas which is gas to be measured and includes thermistors Rd1 to Rd3, a fixed resistor R1, and heater resistors MH1 and MH2. The thermistors Rd1 to Rd3 are each a detection element made of a material having a negative resistance temperature coefficient, such as a composite metal oxide, amorphous silicon, polysilicon, or germanium. The thermistors Rd1 and Rd2 are both configured to detect the concentration of $CO_2$ gas but have mutually different operating temperatures as described later. The thermistor Rd3 functions as a temperature sensor for detecting environmental temperature.

As illustrated in FIG. 1, the thermistors Rd1 and Rd2 are connected in series between a wire supplied with a power supply potential Vcc and a wire supplied with a ground potential GND. The thermistor Rd1 is heated to, for example, 300° C. by the heater resistor MH1, and the thermistor Rd2 is heated to, for example, 150° C. by the heater resistor MH2. The thermistor Rd1 is designed to have a predetermined resistance value when heated to 300° C., and the thermistor Rd2 is designed to have a predetermined resistance value when heated to 150° C. A gas detection signal Vco2_1 appears at the connection point between the thermistors Rd1 and Rd2.

When $CO_2$ gas is present in the measuring atmosphere in a state where the thermistor Rd2 as a detection element is heated to 150° C., the heat dissipation characteristics of the thermistor Rd2 change in accordance with the concentration of $CO_2$ gas. This change appears as a change in the resistance value of the thermistor Rd2. On the other hand, when $CO_2$ gas is present in the measuring atmosphere in a state where the thermistor Rd1 as a reference element is heated to 300° C., the heat dissipation characteristics of the thermistor Rd1 hardly change in accordance with $CO_2$ gas concentration. Accordingly, a change in the resistance value of the thermistor Rd1 heated to 300° C. in accordance with $CO_2$ gas concentration is sufficiently smaller than a change in the resistance value of the thermistor Rd2 heated to 150° C. in accordance with $CO_2$ gas concentration and may be imperceptible. The gas detection signal co2_1 appearing at the connection point between the thermistors Rd1 and Rd2 is supplied to the control circuit 20.

The thermistor Rd3 and a fixed resistor R1 are connected in series between a wire supplied with a power supply potential Vcc and a wire supplied with a ground potential GND. A temperature detection signal Vtemp_1 appears at the connection point between the fixed resistor R1 and the thermistor Rd3. The temperature detection signal Vtemp_1 is input to the control circuit 20.

The control circuit 20 has amplifiers 21 and 22, an AD converter (ADC) 23, a DA converter (DAC) 24, and a control circuit 25. The amplifier 21 amplifies the temperature detection signal Vtemp_1 to generate a temperature detection signal Vtemp_2. The amplifier 22 amplifies the gas detection signal Vco2_1 to generate a gas detection signal Vco2_2. The temperature detection signal Vtemp_2 and gas detection signal Vco2_2 are input to the AD converter 23. The AD converter 23 AD-converts the temperature detection signal Vtemp_2 and gas detection signal Vco2_2 to generate a digital temperature detection value Vtemp_adc and a digital gas detection value Vco2_adc. The temperature detection value Vtemp_adc and gas detection value Vco2_adc are supplied to the control circuit 25. As described above, the control circuit 25 performs calculation and correction based on the gas detection value Vco2_adc to generate an output signal OUT indicating the concentration of $CO_2$ gas. On the other hand, the DA converter 24 DA-converts the digital values supplied from the control circuit 25 to generate heater voltages Vmh1 and Vmh2. The heater voltages Vmh1 and Vmh2 are applied to the heater resistors MH1 and MH2, respectively, to thereby heat the thermistors Rd1 and Rd2.

The following describes a calculation operation of the output signal OUT performed by the control circuit 25.

Figure 2:
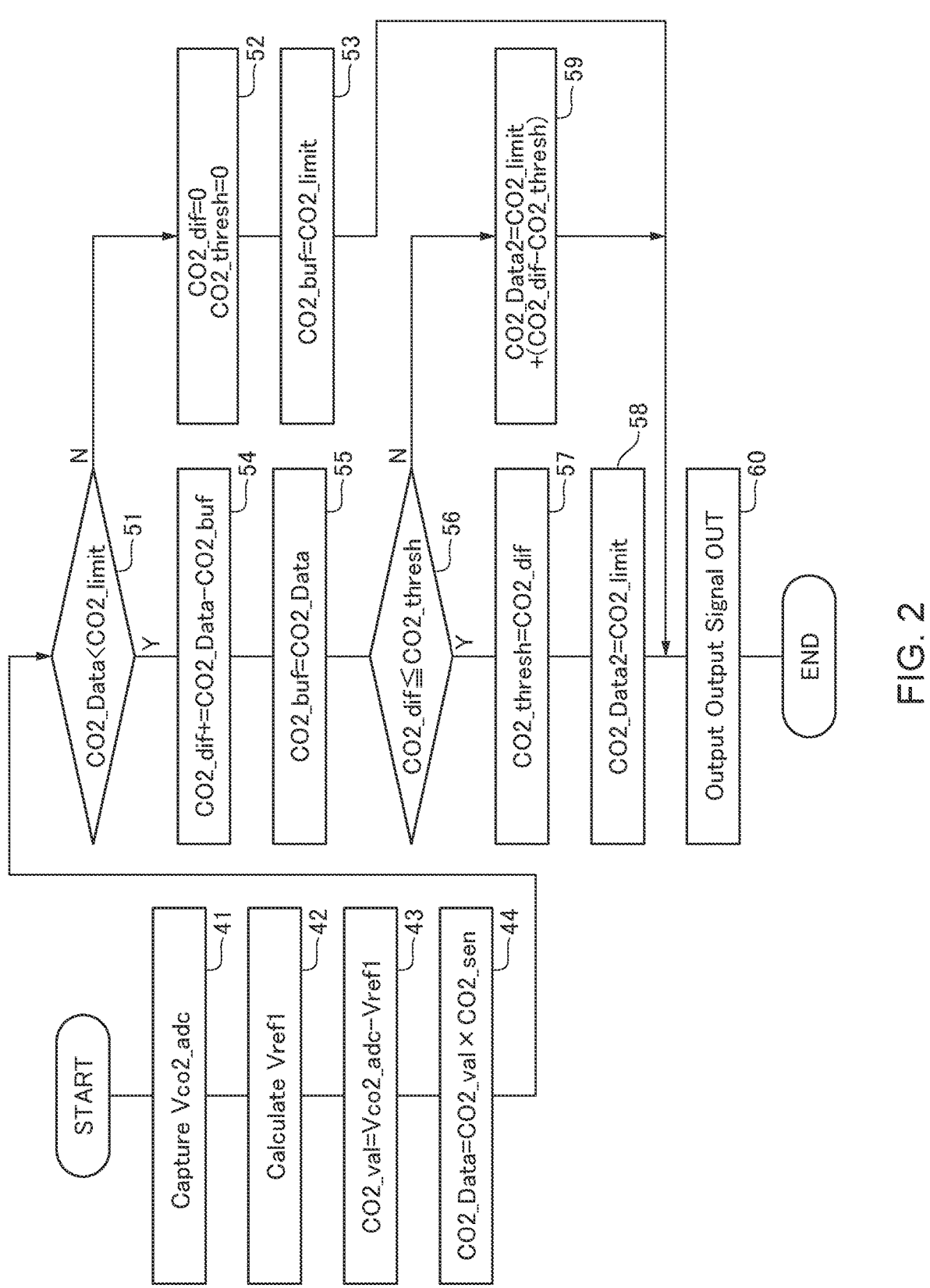
FIG. 2 is a flowchart for explaining a calculation operation of the output signal OUT performed by the control circuit 25.

FIG. 2 is a flowchart for explaining a calculation operation of the output signal OUT performed by the control circuit 25.

The control circuit 25 takes in the gas detection value Vco2_adc (step 41) and calculates a reference value Vref1 (step 42). The reference value Vref1 corresponds to a level obtained as a result of AD-conversion of the gas detection signal Vco2_2 when the concentration of the gas to be measured is a value obtained in normal time. In other words, the value of the gas detection value Vco2_adc to be originally input to the control circuit 25 when the concentration of the gas to be measured is a value obtained in normal time is the reference value Vref1. In the present embodiment, the gas to be measured is $CO_2$ gas, and the concentration of $CO_2$ gas in the atmosphere is about 400 ppm. The concentration of (e.g., 400 ppm) of $CO_2$ gas indicated by the reference value Vref1 is stored as a limit value CO2_limit in a memory 31 provided in the control circuit 25.

Figure 3:
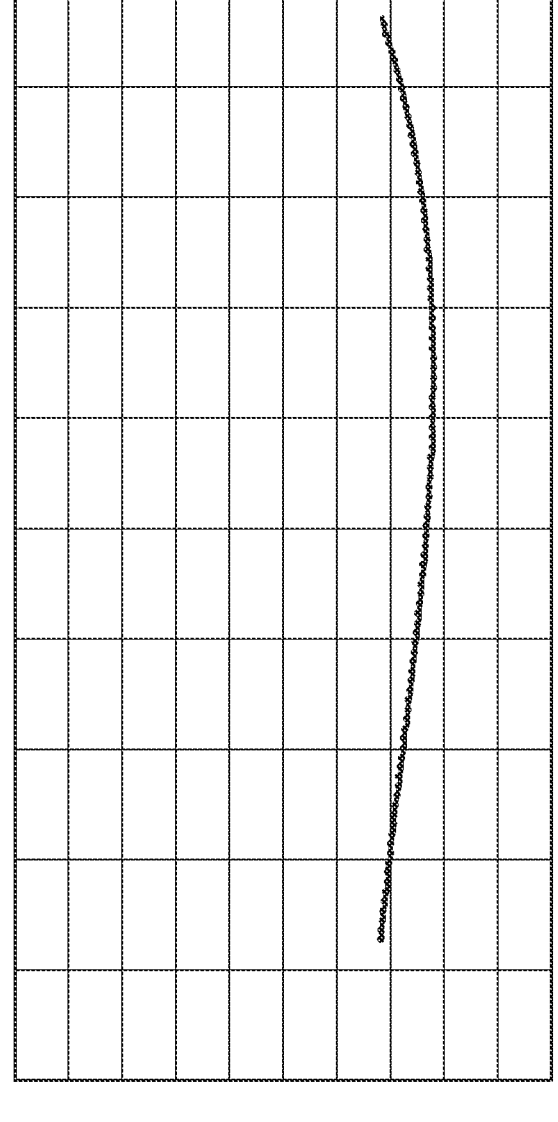
FIG. 3 is a graph showing the relationship between the environmental temperature and the reference value Vref1.

As illustrated in FIG. 3, the reference value Vref1 may differ depending on environmental temperature. Thus, for more accurate measurement, the control circuit 25 calculates the reference value Vref1 in accordance with the current environmental temperature with reference to the temperature detection value Vtemp_adc. The execution order of steps 41 and 42 may be reversed. The control circuit 25 need not execute step 42 every time it takes in the gas detection value Vco2_adc and may execute steps 41 and 42 at different periods or asynchronously. Further, it is not essential that the reference value Vref1 is calculated in accordance with environmental temperature, and when a change in the reference value Vref1 attributable to environmental temperature is small, the reference value Vref1 to be used may be set irrespective of environmental temperature. In this case, a prescribed reference value Vref1 may be stored in the memory 31 provided in the control circuit 25 so as to allow the reference value Vref1 to be read out therefrom in step 42. Further, the control circuit 25 may periodically execute calibration operation of calibrating drift of the reference value Vref1 caused due to a temporal change. Even when the reference value Vref1 is stored in the memory 31, the reference value Vref1 may be updated as needed by the calibration operation.

Then, the control circuit 25 calculates a difference value CO2_val between the gas detection value Vco2_adc and the reference value Vref1 (step 43) and then multiplies the difference value CO2_val by a sensitivity coefficient CO2_sen to calculate a gas concentration value CO2_Data (step 44). The gas concentration value CO2_Data corresponds to the concentration of $CO_2$ gas before correction.

Then, the control circuit 25 compares the calculated gas concentration value CO2_Data and limit value CO2_limit stored in the memory 31 (step 51). When the gas concentration value CO2_Data is equal to or more than the limit value CO2_limit (N in step 51), the control circuit 25 resets a difference value CO2_dif stored in a memory 33 and a threshold value CO2_thresh stored in a memory 34 to 0 (step 52), overwrites a buffer value CO2_buf stored in the memory 32 with the limit value CO2_limit (step 53), and outputs the gas concentration value CO2_Data as the output signal OUT (step 60). Steps 52, 53, and 60 may be executed in a desired order.

On the other hand, when the gas concentration value CO2_Data is less than the limit value CO2_limit (Y in step 51), the control circuit 25 adds the difference between the gas concentration value CO2_Data and the buffer value CO2_buf to the difference value CO2_dif stored in the memory 33, overwrites the resultant value in the memory 33 (step 54), and overwrites the buffer value CO2_buf stored in the memory 32 with the gas concentration value CO2_Data (step 55). The limit value CO2_limit indicates the concentration (e.g., 400 ppm) of $CO_2$ gas in the atmosphere obtained in normal time, and it is unlikely that $CO_2$ gas concentration is less than the limit value CO2_limit under normal circumstances. That is, the case where the gas concentration value CO2_Data is less than the limit value CO2_limit (Y in step 51) means that the gas detection signal Vco2_1 indicates an abnormal value due to negative drift caused in the thermistors Rd1 and Rd2.

Then, the control circuit 25 determines whether the difference value CO2_dif stored in the memory 33 is equal to or less than the threshold value CO2_thresh stored in the memory 34 (step 56). When the difference value CO2_dif is equal to or less than the threshold value CO2_thresh (Y in step 56), the control circuit 25 overwrites the threshold value CO2_thresh stored in the memory 34 with the difference value CO2_dif (step 57), sets the limit value CO2_limit as it is to a gas concentration value CO2_Data2 (step 58), and outputs the gas concentration value CO2_Data2 as the output signal OUT (step 60). On the other hand, when the difference value CO2_dif exceeds the threshold value CO2_thresh (N in step 56), the control circuit 25 sets a value obtained by adding the difference between the difference value CO2_dif and the threshold value CO2_thresh to the limit value CO2_limit to the gas concentration value CO2_Data2 (step 59) and outputs the gas concentration value CO2_Data2 as the output signal OUT (step 60).

As described above, when the gas concentration value CO2_Data is less than the limit value CO2_limit, the control circuit 25 generates the corrected gas concentration value CO2_Data2. Thus, the output signal OUT is corrected to be higher than $CO_2$ gas concentration indicated by the gas detection signal Vco2_1.

The following describes a specific example of a correction operation of the output signal OUT performed by the control circuit 25.

Figure 4:
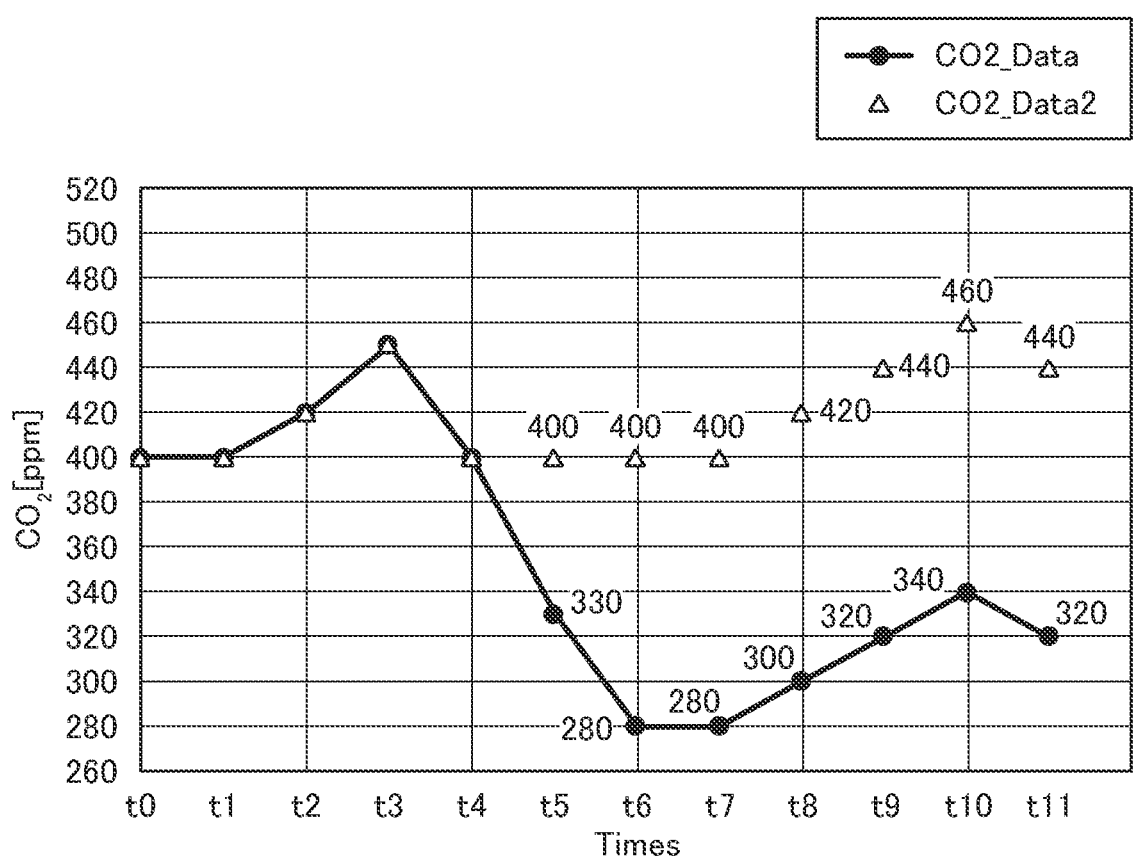
FIG. 4 is a graph for explaining a specific example of a correction operation of the output signal OUT performed by the control circuit 25.

FIG. 4 is a graph for explaining a specific example of a correction operation of the output signal OUT performed by the control circuit 25. In the example illustrated in FIG. 4, the limit value CO2_limit stored in the memory 31 is set to 400 ppm. The initial value of the buffer value CO2_buf stored in the memory 32 is the same (400 ppm) as the limit value CO2_limit. The initial values of the difference value CO2_dif and threshold value CO2_thresh stored in the memory 33 and memory 34, respectively, are both 0 ppm.

During the period from time t0 to t4, the gas concentration value CO2_Data is equal to or more than 400 ppm as the limit value CO2_limit (N in step 51), so that the detected gas concentration value CO2_Data is not corrected but output as it is as the output signal OUT (step 60). In this period, the buffer value CO2_buf is maintained at 400 ppm, and the difference value CO2_dif and the threshold value CO2_thresh are both maintained at 0 ppm.

At time t5, the gas concentration value CO2_Data indicates 330 ppm which is less than 400 ppm as the limit value CO2_limit (Y in step 51). As a result, the difference value CO2_dif is updated to –70 ppm (=330 ppm–400 ppm) (step 54), and the buffer value CO2_buf is updated to 330 ppm (step 55). Since the difference value CO2_dif is equal to or less than threshold value CO2_thresh (=0 ppm) (Y in step 56), the threshold value CO2_thresh is overwritten with the difference value CO2_dif (step 57), and the gas concentration value CO2_Data2 is corrected to 400 ppm as the limit value CO2_limit (step 58) and output as the output signal OUT (step 60). As described above, when the gas concentration value CO2_Data is less than the 400 ppm as the limit value CO2_limit, the output signal OUT is corrected so as to be higher than $CO_2$ gas concentration that has actually been detected.

At time t6, the gas concentration value CO2_Data indicates 280 ppm which is less than 400 ppm as the limit value CO2_limit (Y in step 51). As a result, the difference value CO2_dif is updated to –120 ppm (=–70 ppm+280 ppm–330 ppm) (step 54), and the buffer value CO2_buf is updated to 280 ppm (step 55). Since the difference value CO2_dif is equal to or less than threshold value CO2_thresh (=–70 ppm) (Y in step 56), the threshold value CO2_thresh is overwritten with the difference value CO2_dif (step 57), and the gas concentration value CO2_Data2 is corrected to 400 ppm as the limit value CO2_limit (step 58) and output as the output signal OUT (step 60).

At time t7, the gas concentration value CO2_Data indicates 280 ppm which is less than 400 ppm as the limit value CO2_limit (Y in step 51). As a result, the difference value CO2_dif is updated to –120 ppm (=–120 ppm+280 ppm–280 ppm) (step 54), and the buffer value CO2_buf is updated to 280 ppm (step 55). Since the difference value CO2_dif is equal to or less than threshold value CO2_thresh (=–120 ppm) (Y in step 56), the threshold value CO2_thresh is overwritten with the difference value CO2_dif (step 57), and the gas concentration value CO2_Data2 is corrected to 400 ppm as the limit value CO2_limit (step 58) and output as the output signal OUT (step 60).

As described above, when the gas concentration value CO2_Data is changed from a value equal to or more than 400 ppm as the limit value CO2_limit to a value less than 400 ppm (time t4→time t5), the output signal OUT is corrected to 400 ppm as the limit value CO2_limit. Further, even when $CO_2$ gas concentration further decreases after the gas concentration value CO2_Data falls below 400 ppm as the limit value CO2_limit (time t5→time t6), the decrease is not reflected in the output signal OUT, but the output signal OUT is fixed to 400 ppm as the limit value CO2_limit.

At time t8, the gas concentration value CO2_Data indicates 300 ppm which is less than 400 ppm as the limit value CO2_limit (Y in step 51). As a result, the difference value CO2_dif is updated to –100 ppm (=–120 ppm+300 ppm–280 ppm) (step 54), and the buffer value CO2_buf is updated to 300 ppm (step 55). Since the difference value CO2_dif exceeds the threshold value CO2_thresh (=–120 ppm) (N in step 56), a value obtained by adding the difference (=20 ppm) between the difference value CO2_dif and the threshold value CO2_thresh to the limit value CO2_limit becomes the gas concentration value CO2_Data2 (step 59), which is output as the output signal OUT (step 60). In this case, the output signal OUT indicates 420 ppm. As described above, when a change in the level of the gas detection signal Vco2_1 indicates an increase in $CO_2$ gas concentration (time t7→time t8) during a period when the gas concentration value CO2_Data is less than 400 ppm as the limit value CO2_limit, the increase (20 ppm, in this case) is reflected in the output signal OUT.

The same applies to time t9 and time t10. That is, the gas concentration value CO2_Data indicates 320 ppm and 340 ppm at time t9 and t10, respectively, both of which are less than 400 ppm as the limit value CO2_limit; however, a change in the level of the gas detection signal Vco2_1 indicates an increase in $CO_2$ gas concentration, so that the increase (20 ppm, at both time t9 and t10) is reflected in the output signal OUT. As a result, the output signal OUT indicates 440 ppm at time t9 and 460 ppm at time t10.

At time t11, the gas concentration value CO2_Data indicates 320 ppm which is less than 400 ppm as the limit value CO2_limit (Y in step 51). As a result, the difference value CO2_dif is updated to –80 ppm (=–60 ppm+320 ppm–340 ppm) (step 54), and the buffer value CO2_buf is updated to 320 ppm (step 55). Since the difference value CO2_dif exceeds the threshold value CO2_thresh (=–120 ppm) (N in step 56), a value obtained by adding the difference (=40 ppm) between the difference value CO2_dif and the threshold value CO2_thresh to the limit value CO2_limit becomes the gas concentration value CO2_Data2 (step 59), which is output as the output signal OUT (step 60). In this case, the output signal OUT indicates 440 ppm. As described above, when a change in the level of the gas detection signal Vco2_1 indicates a decrease in $CO_2$ gas concentration (time t10→time t11) during a period when the gas concentration value CO2_Data is less than 400 ppm as the limit value CO2_limit, the decrease (20 ppm, in this case) is reflected in the output signal OUT within a range not less than the limit value CO2_limit.

Figure 5:
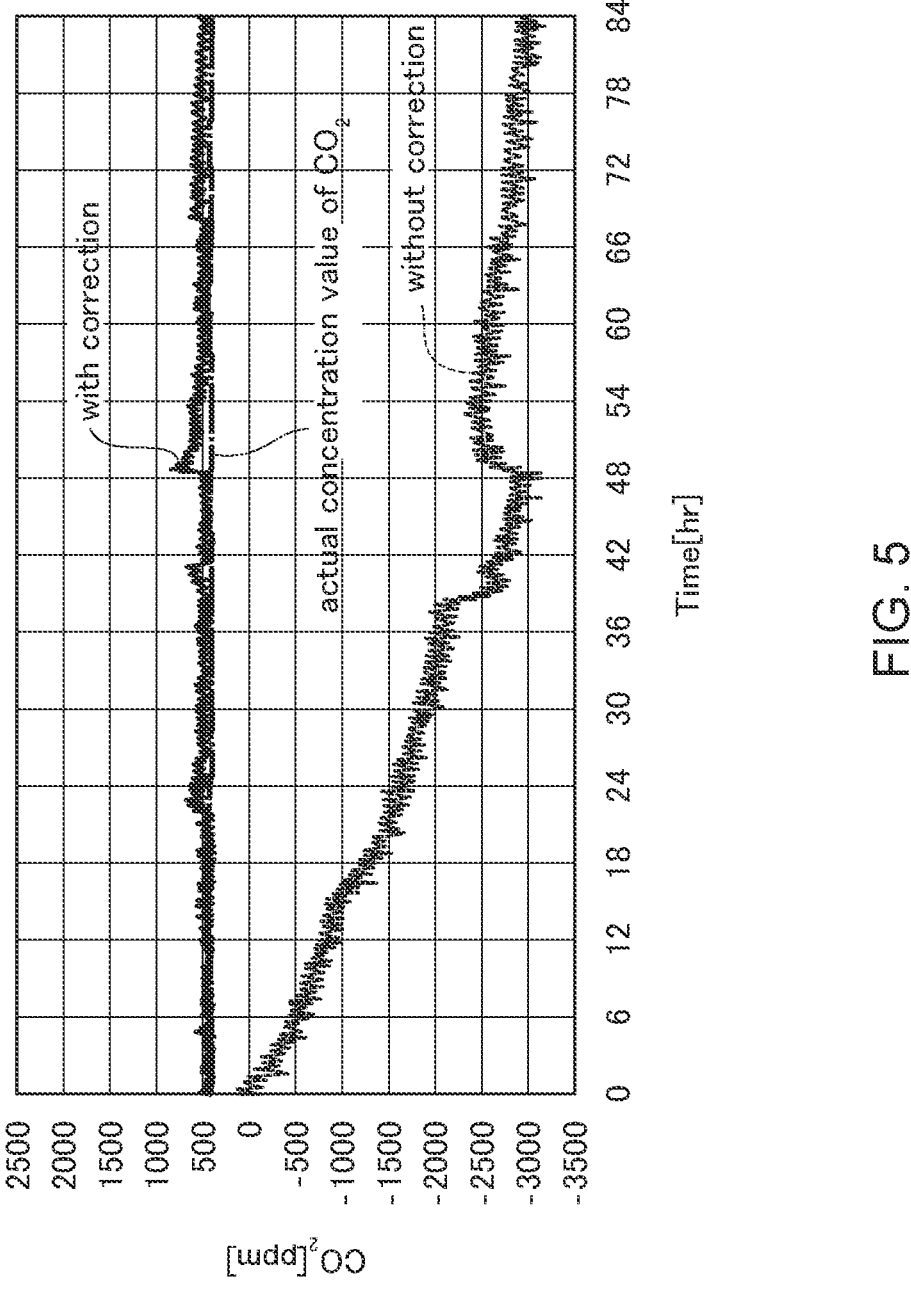
FIG. 5 is a graph illustrating actual measurement values for explaining effects of the gas sensor 1.

FIG. 5 is a graph illustrating actual measurement values for explaining effects of the gas sensor 1 according to the present embodiment.

As can be seen from FIG. 5, when the correction is not performed, $CO_2$ gas concentration indicated by the output signal OUT decreases with the elapse of time and has a negative value even under the condition where $CO_2$ gas concentration in the atmosphere is constant at 400 ppm. On the other hand, in the gas sensor 1 according to the present embodiment, the correction is executed when the gas concentration value CO2_Data is less than the limit value CO2_limit, so that negative drift caused in the thermistors Rd1 and Rd2 is corrected in real time, thereby allowing a correct concentration value of $CO_2$ gas to be output.

While the preferred embodiment of the present disclosure has been described, the present disclosure is not limited to the above embodiment, and various modifications may be made within the scope of the present disclosure, and all such modifications are included in the present disclosure.

For example, although $CO_2$ gas is used as the gas to be measured in the above embodiment, the present invention is not limited to this. Further, the sensor part used in the present invention need not necessarily be a heat conduction type sensor and may be a sensor of another type such as a contact combustion type. For example, when CO gas is the gas to be measured, a sensor part of a contact combustion type can be used. The concentration of CO gas is substantially 0 in normal time, so that when CO gas is the gas to be measured, the limit value stored in the memory 31 may be set to 0 ppm.

The technology according to the present disclosure includes the following configuration examples but not limited thereto.

A gas sensor according to the present disclosure includes a sensor part that generates a gas detection signal in accordance with the concentration of the gas to be measured and a control circuit that generates an output signal indicating the concentration of the gas to be measured based on the gas detection signal. The control circuit corrects the concentration of the gas to be measured indicated by the gas detection signal when the level of the gas detection signal output from the sensor part is less than a reference value corresponding to the level of the gas detection signal, which is normally obtained when the concentration of the gas to be measured is a concentration value in normal time, and thus indicates a value lower than the actual concentration value of the gas to be measured in the atmosphere to thereby bring the concentration of the gas to be measured indicated by the output signal close to the actual concentration value in the atmosphere. This configuration makes it possible to cancel negative drift in real time.

In the above gas sensor, when the level of the gas detection signal output from the sensor part is changed from a value equal to or more than the reference value to a value less than the reference value, the control circuit may correct the output signal such that it indicates the concentration value in normal time. This prevents the concentration of the gas to be measured indicated by the output signal from falling below the concentration value in normal time.

In the above gas sensor, when a change in the level of the gas detection signal output from the sensor part indicates an increase in the concentration of the gas to be measured in a period when the level of the gas detection signal output from the sensor part is less than the reference value, the control circuit may reflect the increase in the output signal. Thus, the increase in the gas concentration is reflected in the output signal without being cancelled even during a correction period.

In the above gas sensor, when a change in the level of the gas detection signal output from the sensor part indicates a decrease in the concentration of the gas to be measured in a period when the level of the gas detection signal output from the sensor part is less than the reference value, the control circuit may reflect the decrease in the output signal within a range not less than the concentration value in normal time. Thus, the decrease in the gas concentration is reflected in the output signal without being cancelled even during a correction period.

In the above gas sensor, the control circuit may calculate the reference value every time it takes in the gas detection signal. Thus, even when the reference value is changeable, a more accurate value can be used as the reference value.

In the above gas sensor, the control circuit may calculate the reference value in accordance with environmental temperature. Thus, even when the reference value differs depending on environmental temperature, a more accurate value can be used as the reference value.

In the above gas sensor, the gas to be measured may be $CO_2$ gas, and the concentration in normal time may be the concentration of $CO_2$ gas in the atmosphere in normal time. Thus, there can be provided a $CO_2$ gas sensor capable of cancelling negative drift in real time.

What is claimed is:

1. A gas sensor comprising:
a sensor part configured to generate a gas detection signal in accordance with a concentration of a gas to be measured; and
a control circuit configured to generate an output signal indicating the concentration of the gas to be measured based on the gas detection signal,
wherein the control circuit is configured to correct the output signal so that the output signal indicates a concentration of the gas to be measured higher than that indicated by the gas detection signal when a level of the gas detection signal output from the sensor part is less than a reference value corresponding to a level of the gas detection signal which is normally obtained when a concentration of the gas to be measured is a concentration value in normal time, and
wherein the control circuit is configured to correct the output signal such that the output signal indicates the concentration value in normal time when the level of the gas detection signal output from the sensor part is changed from a value equal to or more than the reference value to a value less than the reference value.

2. The gas sensor as claimed in claim 1, wherein, when a change in the level of the gas detection signal output from the sensor part indicates an increase in a concentration of the gas to be measured in a period when the level of the gas detection signal output from the sensor part is less than the reference value, the control circuit is configured to reflect the increase in the output signal.

3. The gas sensor as claimed in claim 1, wherein, when a change in the level of the gas detection signal output from the sensor part indicates a decrease in a concentration of the gas to be measured in a period when the level of the gas detection signal output from the sensor part is less than the reference value, the control circuit is configured to reflect the decrease in the output signal within a range not less than the concentration value in normal time.

4. The gas sensor as claimed in claim 1, wherein the control circuit is configured to calculate the reference value every time the control circuit takes in the gas detection signal.

5. The gas sensor as claimed in claim 1, wherein the control circuit is configured to calculate the reference value in accordance with environmental temperature.

6. The gas sensor as claimed in claim 1,
wherein the gas to be measured is $CO_2$ gas, and
wherein the concentration in normal time is a concentration of $CO_2$ gas in an atmosphere in normal time.

7. A gas sensor comprising:
a sensor part configured to generate a gas detection signal in accordance with a concentration of a gas to be measured; and
a control circuit configured to generate an output signal indicating the concentration of the gas to be measured based on the gas detection signal,
wherein the control circuit is configured to correct the output signal so that the output signal indicates a concentration of the gas to be measured higher than that indicated by the gas detection signal when a level of the gas detection signal output from the sensor part is less than a reference value corresponding to a level of the gas detection signal which is normally obtained when a concentration of the gas to be measured is a concentration value in normal time, and wherein, when a change in the level of the gas detection signal output from the sensor part indicates a decrease in a concentration of the gas to be measured in a period when the level of the gas detection signal output from the sensor part is less than the reference value, the control circuit is configured to reflect the decrease in the output signal within a range not less than the concentration value in normal time.

8. The gas sensor as claimed in claim 7, wherein, when a change in the level of the gas detection signal output from the sensor part indicates an increase in a concentration of the gas to be measured in a period when the level of the gas detection signal output from the sensor part is less than the reference value, the control circuit is configured to reflect the increase in the output signal.

9. The gas sensor as claimed in claim 7, wherein the control circuit is configured to calculate the reference value every time the control circuit takes in the gas detection signal.

10. The gas sensor as claimed in claim 7, wherein the control circuit is configured to calculate the reference value in accordance with environmental temperature.

11. The gas sensor as claimed in claim 7, wherein the gas to be measured is $CO_2$ gas, and wherein the concentration in normal time is a concentration of $CO_2$ gas in an atmosphere in normal time.

12. A gas sensor comprising:

a sensor part configured to generate a gas detection signal in accordance with a concentration of a gas to be measured; and a control circuit configured to generate an output signal indicating the concentration of the gas to be measured based on the gas detection signal, wherein the control circuit is configured to correct the output signal so that the output signal indicates a concentration of the gas to be measured higher than that indicated by the gas detection signal when a level of the gas detection signal output from the sensor part is less than a reference value corresponding to a level of the gas detection signal which is normally obtained when a concentration of the gas to be measured is a concentration value in normal time, and wherein the control circuit is configured to calculate the reference value every time the control circuit takes in the gas detection signal.

13. The gas sensor as claimed in claim 12, wherein, when a change in the level of the gas detection signal output from the sensor part indicates an increase in a concentration of the gas to be measured in a period when the level of the gas detection signal output from the sensor part is less than the reference value, the control circuit is configured to reflect the increase in the output signal.

14. The gas sensor as claimed in claim 12, wherein the control circuit is configured to calculate the reference value in accordance with environmental temperature.

15. The gas sensor as claimed in claim 12, wherein the gas to be measured is $CO_2$ gas, and wherein the concentration in normal time is a concentration of $CO_2$ gas in an atmosphere in normal time.

* * * * *